United States Patent [19]
Zuest

[11] Patent Number: 5,591,029
[45] Date of Patent: Jan. 7, 1997

[54] DENTAL IMPLANT SYSTEM

[75] Inventor: Max Zuest, San Diego, Calif.

[73] Assignee: Zest Anchors, Inc., Escondido, Calif.

[21] Appl. No.: 102,353

[22] Filed: Aug. 5, 1993

Related U.S. Application Data

[63] Continuation-in-part of Ser. No. 861,183, Mar. 31, 1992, abandoned, which is a continuation of Ser. No. 751,661, Aug. 22, 1991, Pat. No. 5,254,005, which is a continuation of Ser. No. 436,432, Nov. 14, 1989, abandoned.

[51] Int. Cl.$^6$ .................................................... A61C 8/00
[52] U.S. Cl. ............................................ 433/173; 433/174
[58] Field of Search ................................. 433/172, 173, 433/174

[56] References Cited

U.S. PATENT DOCUMENTS

| | | | |
|---|---|---|---|
| 2,112,007 | 3/1938 | Adams | 32/2 |
| 3,499,222 | 3/1970 | Linkow et al. | |
| 3,514,858 | 6/1970 | Silverman | 433/174 |
| 3,656,236 | 4/1972 | Kurer | |
| 3,905,109 | 9/1975 | Cohen et al. | 433/174 |
| 4,177,562 | 12/1979 | Miller et al. | 433/174 |
| 4,431,416 | 2/1984 | Niznick | 433/174 |
| 4,488,875 | 12/1984 | Niznick | 433/173 |
| 4,531,915 | 7/1985 | Tatum, Jr. | 433/173 |
| 4,645,453 | 2/1987 | Niznick | 433/173 |
| 4,713,003 | 12/1987 | Symington et al. | 433/173 |
| 4,713,004 | 12/1987 | Linkow et al. | 433/174 |
| 4,738,622 | 4/1988 | Kawahara et al. | 433/169 |
| 4,744,755 | 5/1988 | Ross | 433/173 |
| 4,762,492 | 8/1988 | Nagai | 433/174 |
| 4,854,872 | 8/1989 | Detsch | 433/173 |
| 4,856,994 | 8/1989 | Lazzara et al. | 433/173 |
| 4,906,191 | 3/1990 | Söderberg | 433/213 |
| 4,907,969 | 3/1990 | Ward | 433/173 |
| 4,932,868 | 6/1990 | Linkow et al. | 433/174 |
| 5,007,835 | 4/1991 | Valen | 433/174 |
| 5,022,860 | 6/1991 | Lazzara et al. | 433/174 |
| 5,078,607 | 1/1992 | Niznick | 433/174 |
| 5,195,891 | 3/1993 | Sulc | 433/173 |
| 5,209,659 | 5/1993 | Friedman et al. | 433/173 |
| 5,246,369 | 9/1993 | Poulmaire | 433/173 |
| 5,468,149 | 11/1995 | D'Alise | 433/173 |

FOREIGN PATENT DOCUMENTS

| | | |
|---|---|---|
| 2635964 | 3/1990 | France . |
| WO9312733 | 7/1993 | WIPO . |

Primary Examiner—Cary E. O'Connor
Attorney, Agent, or Firm—Brown, Martin, Haller & McClain

[57] ABSTRACT

A dental implant assembly is provided, as well as a system and method for exposing an embedded implant after osseointegration has taken place. The implant assembly comprises an implant member for embedding in the jaw and a rest factor member for securing to the implant member, the rest factor member having an upper rest surface just above the tissue level for opposing an overlying portion of a prosthesis anchored elsewhere in the jaw to form a non-retentive rest or support for accepting down pressure from the prosthesis. The implant member is relatively short and can be installed in distal jaw regions without interference with the mandibular nerve. A bore is cut out in the jaw for receiving the implant, inserting the implant and an attached healing screw in the implant. The implant site is closed and osseointegration takes place over an extended period. Subsequently, the implant site is uncovered, the healing screw is removed, and the rest factor member is secured in the implant.

45 Claims, 6 Drawing Sheets

DENTAL IMPLANT SYSTEM

CROSS-REFERENCES TO RELATED APPLICATIONS

This application is a Continuation-In-Part of application Ser. No. 07/861,183 filed Mar. 31, 1992, abandoned, which was a Continuation of application Ser. No. 07/751,661 filed Aug. 22, 1991, now U.S. Pat. No. 5,254,005, which was a Continuation of application Ser. No. 07/436,432 filed Nov. 14, 1989 (now abandoned).

BACKGROUND OF THE INVENTION

The present invention relates to a dental implant system.

Dental implants are embedded in the jaw bone and serve to anchor one or more artificial teeth or dentures. Most implant systems involve a relatively long implant cylinder which is placed into a custom bored hole in the jawbone, then left for several months to allow healing and bone integration. Then the implant must be exposed for attachment of a dental prosthetic appliance such as a crown, denture, partial denture or bridge. This generally involves the dentist cutting out a flap of tissue which is peeled back to expose the implant, and secured by sutures after installing the prosthesis. This results in a relatively large area of trauma with a certain degree of pain to the patient and risk of post-operative infection.

Another problem with conventional implants is their length, which makes them difficult to implant in the distal jaw region, where there is insufficient depth to enable their insertion without interference with the mandibular nerve, without the assistance of a dental surgeon to locate the precise position of the nerve and ensure that the implant does not interfere with it. A shorter cylindrical implant would not normally be suitable since it would provide insufficient "hold" and would likely become loosened with time if anchored to a denture or bridge. Also, side to side forces on the implant lead to bone erosion and trauma. Thus, dentures or bridges are often not anchored at the rear of the jaw. However, this has the disadvantage that trauma to the tissue and underlying bone beneath the denture occurs as a result of the denture repeatedly impacting the bone, particularly with long dentures which will tend to tilt or rotate about their attachment or anchor points during chewing or other jaw motions. This biting pressure can result in bone erosion or resorption down to the level of the nerve.

SUMMARY OF THE INVENTION

It is an object of this invention to provide an improved dental implant system and method which is less likely to cause significant tissue trauma and which reduces bone erosion as a result of denture wear.

It is a further object of this invention to provide an improved system and method for exposing an implant site after osseointegration has taken place.

According to a first aspect of the present invention, a dental implant assembly is provided which comprises a first, implant member for implanting in the distal region of the jaw bone, and a second member or rest factor for attachment to the implant member. The two members have cooperating releasable securing devices for releasably securing them together, preferably comprising a screw threaded bore in the implant member and a corresponding threaded portion on the rest factor member. The rest factor member projects up to just above the level of the tissue overlying the jaw bone and has an upper surface opposing an overlying portion of a prosthesis anchored elsewhere in the jaw to form a rest for the prosthesis which accepts down pressure only, and which acts as a support to prevent or restrict bone erosion. The implant member has a selected height less than the depth of the mandibular nerve at the implant site, so that it can be embedded in the bone without risk of interference with the nerve. At the same time, the implant member is as wide as possible, and preferably has the maximum diameter possible according to the width of the patient's alveolar ridge at the implant site. The implant member diameter is preferably selected to be 1 mm less than the available alveolar ridge or bone width at the implant site. Implant members in a range of different heights and diameters are preferably provided to meet the requirements of a range of patients. Preferably, implant members with heights of 2 mm, 4.5 mm, 7 mm and 10 mm are provided, to allow for patients whose jawbone is already eroded to some extent. Implant members with diameters ranging from about 4 mm to 6 mm may be provided.

Since the implant member is of relatively large diameter, it has a relatively large surface area resisting downward forces. In a preferred embodiment of the invention, the implant member has a generally cylindrical body with an upper end portion and downwardly depending stem portion which engages in a corresponding recess drilled out in the bone. Preferably, at least part of the stem portion at the lower end of the implant member has an annular recess forming an outer rim and central boss. This engages a corresponding annular recess drilled out in the bone to resist sideways movement of the implant. This will resist sideways movement of the implant during osseointegration, and also provides additional depth for securing the rest factor to the implant member. A bore of corresponding shape to the undersurface of the implant member is drilled out in the jawbone at the implant site, so that when the implant member is positioned in the bore, the peripheral rim will provide stabilization of the member against lateral movement during the osseointegration period. The shape of the undersurface of the implant provides a large area of bone to implant contact for osseointegration, and significant resistance to both lateral and downward forces both during and after the osseointegration period. Preferably, at least two separate or double lead threads are provided, and triple or quadruple threads may be provided for added retention. Bone grows into the gaps between threads.

The outer surface of the stem portion of the implant preferably has threads to provide additional surface area for bone attachment. Bone grows into the area above and below the threads to resist loosening of the implant.

Since the rest factor is not anchored to the prosthesis, the risk of jaw bone erosion or damage as a result of upward forces is reduced. However, the rest factor does accept down pressure as a result of biting pressure of the denture, and will thus reduce the risk of trauma to the tissue and jawbone erosion as a result of pressure. The localized contact between the rest factor and the underlying bone via the implant member reduces or substantially eliminates pressure trauma on the entire bone.

If desired, the upper surface of the rest factor and the opposing portion of the prosthesis may be provided with opposing, non-retentive mating formations, such as opposing slightly convex and concave formations, for guiding the prosthesis against the rest factor. However, these formations do not provide any upwards retention of the prosthesis. A series of such rest factors may be provided at appropriate locations in the jaw where maximum down pressure from a denture is encountered, considerably reducing the discomfort of denture use and reducing the risk of tissue and jawbone damage as would result from conventionally anchored dentures.

The rest factor may be preformed with a suitable rest surface in incremental heights, in which case the procedure after removing the healing screw comprises selecting an appropriate height rest factor and securing the selected rest factor in the implant member.

The implant member may be relatively short with a relatively large diameter, so that it can be anchored securely in the jawbone without needing a deep bore to be drilled out. The implant member is provided in several heights. The shortest of the implants will be shorter and wider than conventional cylindrical implants, and thus can be used at the back or posterior mandible of the jaw where the nerve position prevents or restricts the use of long implants. This implant is particularly suitable for positioning a rest factor in the second molar area in conjunction with implant dentistry where cantilevered bridges or anterior implants need support or in other places where a rest factor is needed in dentistry. The implant requires less bone to be drilled out than conventional cylindrical implants, reducing or minimizing bone loss, and is able to accept hundreds of pounds of down pressure from an overlying denture or prosthesis.

After bone integration, the implant can be recovered by piercing the tissue overlying a healing screw secured to the implant with a pointed end of a locating guide tool, probing the implant site with the pointed end until it engages a hole in the top of the healing screw, inserting the pointed end into the hole, utilizing a tissue punch centered on the guide tool to cut out a plug of tissue directly over the implant, and subsequently removing the healing screw.

Thus, the locating tool and tissue punch can be removed together from the implant site, carrying with them the tissue plug to expose the healing screw for removal with a separate tool. The implant is then exposed for secondary healing or restoration procedures while a minimum amount of tissue has been disturbed and little or no suturing is required. This considerably reduces the trauma, secondary tissue healing, discomfort to the patient, and risk of infection.

The implant member provides osseointegration with good resistance to loosening forces as a result of chewing. It may alternatively be used to secure other dental devices such as an implant denture anchor or an implant magnet abutment.

An implant locating and exposing tool may be used to recover the implant. The tool comprises an elongate shaft having a head at one end and a locating probe at the opposite end having a sharp end for probing the tissue over an implant site to locate a central hole in the top of a healing screw, and a cutter member mounted on the elongate member with its cutting face facing in the same direction as the locating probe, the cutter member being movable along the elongate shaft to cut out a plug of tissue overlying a healing screw.

Thus, the healing screw can be located and the overlying tissue removed in one step, without having to cut out a relatively large flap of tissue.

The healing screw may be provided with a concave upper surface so that the locating probe will be guided towards the central opening.

The implant system and method described above provides a rest surface for an overlying cantilevered bridge or denture which is anchored elsewhere in the jaw, on which the denture can rest and which accepts down pressure from the denture, reducing tissue trauma. Rest surfaces may be provided wherever needed, in conjunction with the conventional implants and anchors used for securing the denture or prosthesis in the jaw. The improved implant recovery tool and method produces minimal trauma when exposing a previously embedded implant for subsequent connection to either a rest factor or to a conventional anchor or magnet abutment.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENTS

Figures 1, 2, 3, 4A, 4B, 5:
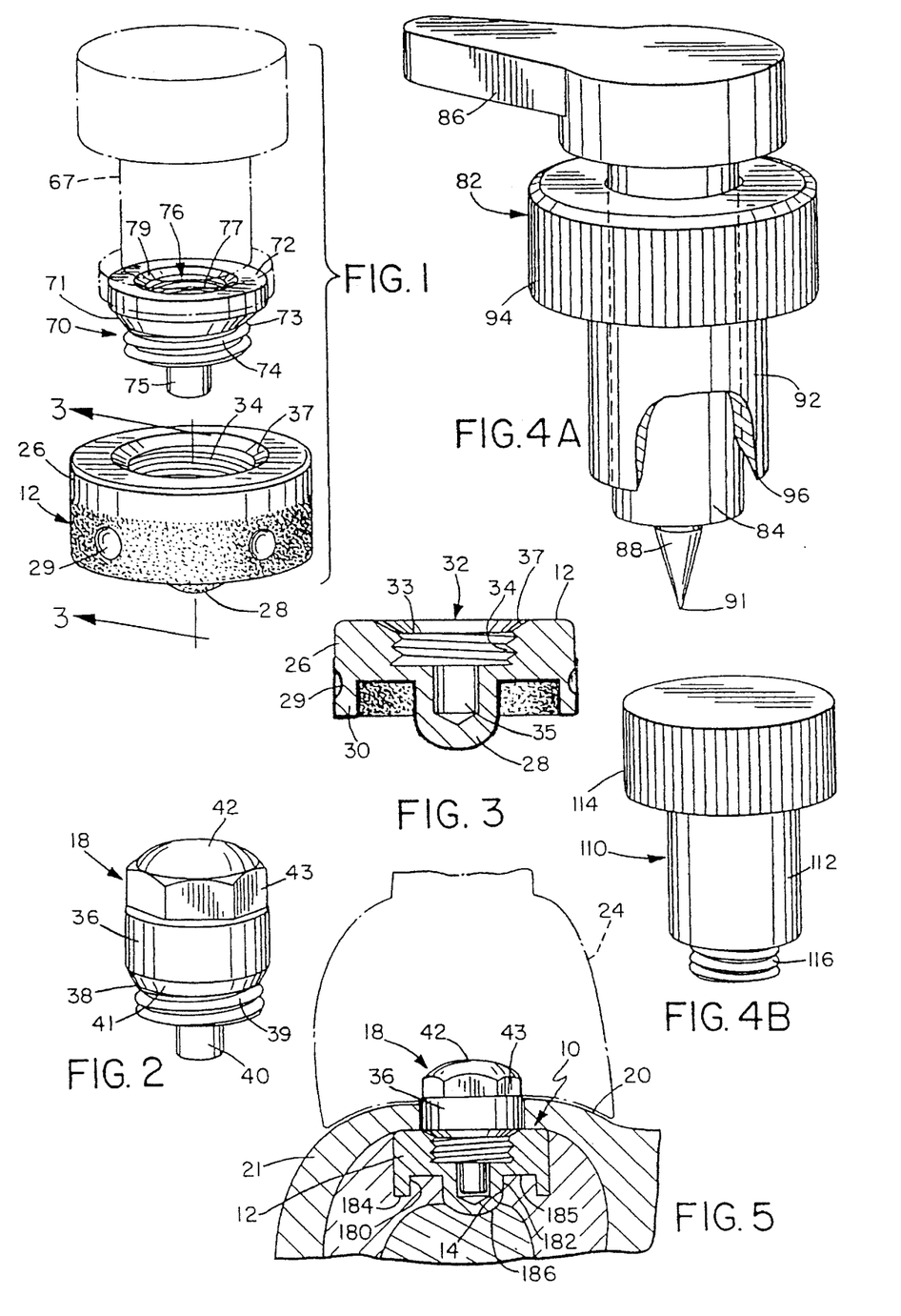
FIG. 1 is a perspective view of the separated implant and healing screw components of an implant assembly according to a preferred embodiment of the invention.
FIG. 2 is a perspective view of a rest factor of the implant assembly.
FIG. 3 is a sectional view of the implant taken on line 3—3 of FIG. 1.
FIG. 4A is a perspective view of a preferred embodiment of the implant locating tool according to another aspect of the invention.
FIG. 4B is a perspective view of a healing screw removal tool.
FIG. 5 is a sectional view through a typical jawbone with a finished implant in place and a rest factor inserted.
Figure 6:
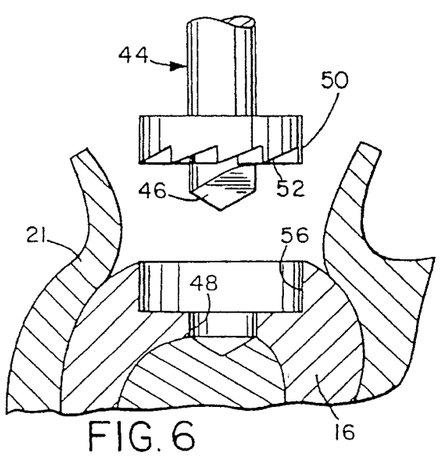
FIG. 6 is a jawbone section illustrating the initial drilling set up for an implant.

FIGS. 1—3 and 5 of the drawings illustrate an implant assembly 10 according to a preferred embodiment of the present invention, as well as a preferred method of installing the assembly in the jaw. As best illustrated in FIG. 5, the implant assembly 10 basically comprises an implant 12 for insertion into a suitably prepared bore 14 in the jawbone 16, where it is secured in place by osseointegration as is known in the field of implant dentistry, and an extension member or rest factor 18 secured to the implant 12 and extending up to slightly above the level 20 of the tissue or gum 21 to form a rest surface 22 for an overlying denture or bridge 24 which is anchored elsewhere in the jaw.

As best illustrated in FIGS. 1 and 3, implant 12 comprises a thin, annular member 26 having a central spigot or downward extension 28 projecting from one of its faces and an annular peripheral rim 30 projecting from the same face. A central bore 32 extends from the opposite face into the spigot 28, as illustrated in FIG. 4. The bore 32 has a larger diameter upper portion 33 having internal screw threads 34 extending along its length with a taper 37 at its upper end for added strength to hold the threaded engagement. The lower end of bore 32 comprises a smaller diameter lower portion 35 extending into spigot 28 for centering parts mating with implant 12 and preventing cross-threading of the threaded engagement. The implant will be of metal or any suitably rigid material as is normally used for dental implants, for example surgical titanium alloy. The implant may have spaced, short grooves or indents 29 on its outer surface for resisting rotation. These are preferably of the order of 1 mm in length.

Figure 11:
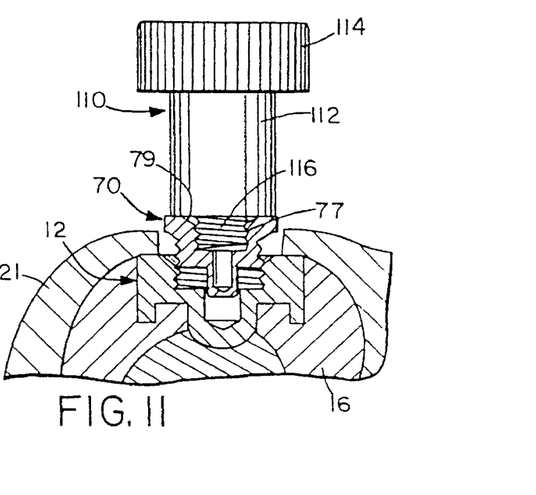
FIG. 11 illustrates the removal of the healing screw.

Also illustrated in FIG. 1 is a healing screw 70 for insertion in the implant member during the osseointegration process. Healing screw 70 has a relatively short head portion 72 and downwardly depending shaft portion 73 for engagement in the bore 32 of implant 12. Portion 73 has a screw threaded larger diameter upper part 74 for threaded engagement in bore portion 33, the upper part 74 having a taper 71 at its upper end matching the taper 37 at the upper end of the implant bore 32 for support and seating of the screw 70 in bore 32. The lower end of portion 73 comprises a smaller diameter, cylindrical lower part 75 for fitting into lower portion 35. The upper end face of the head portion has a central, tool receiving bore 76 for receiving the end of a suitable tool for inserting the arrangement in the bore in the jawbone, and for subsequently receiving the end of a locating or removing tool as will be explained in more detail below. If desired, the upper end face of screw 70 may have a concave or dish-shaped depression 79 surrounding bore 76. The bore corresponding to bore 76 is illustrated in FIG. 11 and has a screw threaded upper portion 77 and a downwardly depending cylindrical centering extension 76 corresponding to extension 75 in FIG. 1. The threads in upper portion 77 are of opposite hand to those of screw threaded portion 74. In the embodiment illustrated in the drawings, portion 74 has a right hand thread while portion 77 has a left hand thread. The healing screw may be provided in a range of sizes, but in each case the height of the head portion is of the order of 1 mm or less.

The extension or rest factor member 18 as it appears prior to installation in the jaw is illustrated in FIG. 2. The member comprises a generally cylindrical boss 36 having a projecting shaft 38 at one end dimensioned for mating engagement in the bore 32 of implant 12. Shaft 38 has an upper, larger diameter portion 39 having external screw threads for threaded engagement with the internal screw threads 34 in the upper part 33 of bore 32, and a lower, smaller diameter cylindrical extension 40 for fitting into the lower part 35 of bore 32, as illustrated in FIG. 11. The upper end of shaft 38 has a taper 41 matching the taper 37 at the upper end of the implant bore 32. Member 18 has a curved, slightly convex rest or support surface 42 at its upper end, and an external hex formation 43 for securing it to a suitable tool for insertion into the implant. The member 18 will also be of a suitable dental material such as titanium alloy.

Member 18 may alternatively be formed with a concave support surface (not illustrated), or with any suitably shaped upper rest or support surface. Member 18 will be made in a range of heights to allow the dentist to select the appropriate size rest factor for a particular patient's tissue level. The rest factor is selected to project only to a distance of the order of ½ to 1 mm above the tissue level when installed in the jaw, and is preferably kept as low as possible so that it acts to accept biting pressures but will not interfere with normal jaw motions.

Figure 12:
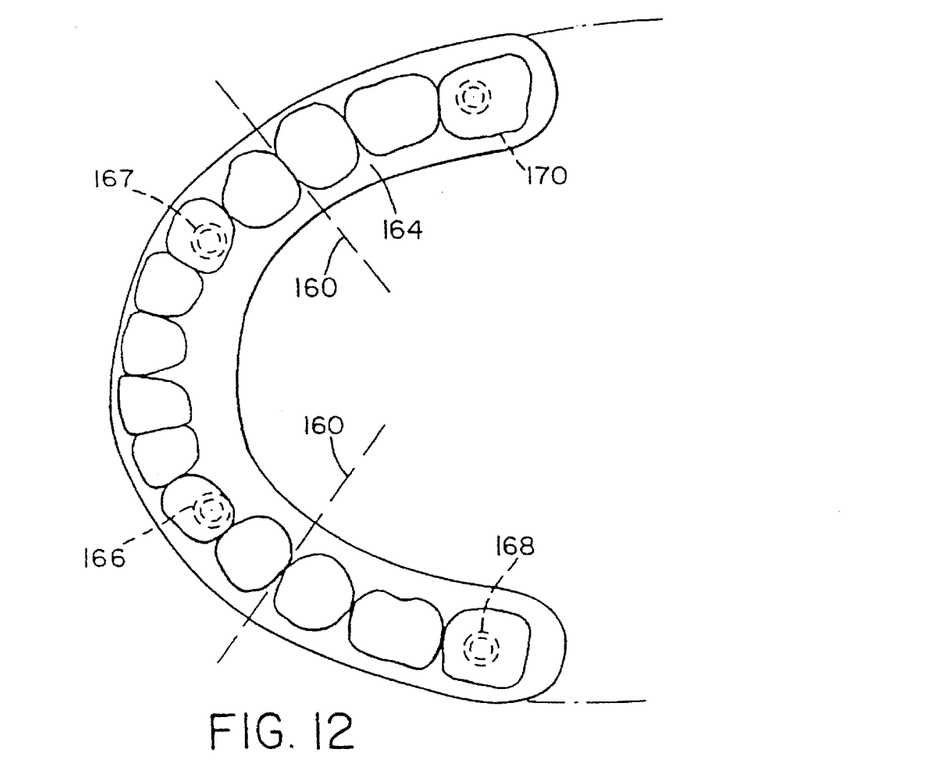
FIG. 12 illustrates the lower half of a patient's jaw with a full denture anchored in place and seated on rest factors in posterior areas on both sides.
Figure 13:
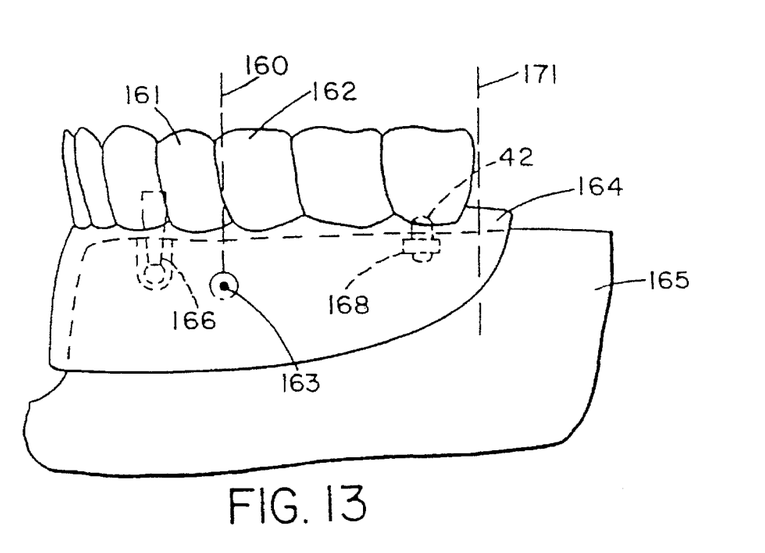
FIG. 13 is a side view of the denture arrangement of FIG. 12.

The implant assembly with the rest surface 42 is used to form a rest or support surface in implant dentistry for a prosthesis anchored elsewhere in the jaw, for example, as illustrated in FIGS. 12 and 13. The implant assembly is designed to be relatively short or thin so that it can be installed in distal jaw regions to the rear of line 160 in FIGS. 12 and 13, which extends between the first and second bicuspids 161 and 162 and corresponds to the approximate location where the mandibular nerve 163 exits the jawbone. The mandibular nerve extends through the jawbone to the rear of the first bicuspid, making the installation of long implants in this region difficult or impossible without the assistance of a dental surgeon. Thus, unsecured dentures are common, resulting in bone erosion from biting impacts. This rest factor assembly avoids or reduces such problems. The implant has a relatively large diameter as compared to its height, providing good implant to bone contact and integration, while having only a short penetration into the jawbone. In the preferred embodiment illustrated, the penetration into jawbone is only between 2 to 4.5 mm, depending on the patient's bone depth, and there is thus no risk of interference with the mandibular nerve.

FIGS. 12 and 13 illustrate the assembly implanted in the jaw for cooperation with an overlying denture anchored elsewhere. In FIGS. 12 and 13, a full denture or prosthesis 164 is illustrated, secured to a patient's lower jaw 165 via a pair of anchors 166, 167 mounted in the anterior regions of the patient's jaw, and seated on implanted rest factors 168, 170 in the posterior or distal jaw region below the former second molar at each end of the denture. In practice, the rest factor assembly may be installed anywhere between the region corresponding to the former second molar (line 171) and the first bicuspid (line 160). The area to the rear of the line 171 has too many muscles for insertion of an implant. As illustrated in FIG. 13, the rest factors may be provided or preformed with a slightly convex or ball-shaped head 42 which projects from around ½ to 1 mm above the tissue level, although support surfaces of a different shape may be provided. The prosthesis or denture is preferably provided with a corresponding concave surface or depression for seating on the opposing rest factors or surfaces 168 and 170.

Most typical denture anchors allow a limited degree of pivoting or side-to-side motions of the denture with jaw motions so as to reduce stress in the jaw bone areas to which the denture is positively anchored. With relatively long partial or full dentures which extend into the posterior jaw regions, tilting or rotation of the denture about the anchor points with jaw or biting motions will apply pressure or biting force to the underlying tissue and jawbone, causing discomfort and trauma to the underlying bone and tissue, and ultimately resulting in significant bone erosion. The rest surface or surfaces avoid or reduce this problem by accepting down or biting pressure from the denture. Since the rest surfaces are not positively anchored to the denture, they will not be pulled up or from side to side as a result of jaw motions, and will therefore be less likely to cause bone erosion or damage. The implant assembly is therefore intended to be used at appropriate locations in the jaw which would otherwise be subject to considerable down pressure and potential trauma from an implant such as a full or partial denture or cantilevered bridge. The rest factor surface will be shaped to ensure that it can accept down pressure from an overlying denture in various possible orientations, whatever the angle of the patient's jaw. The support surface prevents excessive force on the tissue, and thus protects the gum tissue from impacting forces which could cause soreness and trauma. Additionally, the rest or support surface prevents or reduces bone erosion by providing support to the distal end of the denture and resisting biting forces.

The implant assembly is designed for implantation at any position in the jaw where a rest factor or surface for a full or partial denture or bridge is needed. Normally, this will be in the posterior jaw, for example in between the first bicuspid and the second molar area, as illustrated in FIGS. 12 and 13, but a rest surface may also be advantageous in other areas. The dimensions of the assembly 10 are selected according to the dimensions of the jaw in the area where the implant is to be used. A range of implant assemblies of different dimensions may be provided for fitting patients having different jaw dimensions. The implant member is designed to provide sufficient anchoring area with the jawbone when embedded in the jaw, while not extending too deeply into the jaw where it might otherwise interfere with the nerve. The implant member has a relatively large diameter, larger than typical straight cylindrical implants, but is shorter in length than such implants, preferably having an overall length in the range from 2 mm to 4.5 mm. In one specific example, several different size implants were provided with annular members of 4.25 mm, 5 mm, and 6 mm outer diameter, respectively. The rest factor may have a diameter of 4 mm. The extension or spigot 28 may also be provided in different sizes according to the position in the jaw where it is to be embedded. Central spigots of length between 1 mm and 3 mm may be provided. Also, the central spigot may be omitted in some cases where very little depth is available in the jawbone for embedding the implant. In this case, the rest factor 18 will also have no projection 40.

Rest factors having heads in a range of different sizes are also provided, for example, 3 mm, 4 mm and 5 mm. Generally, the overall implant assembly is very short, extending only from 2 to 4.5 mm into the jawbone, while the implant is shaped to have a relatively large bone to implant contact area, as best illustrated in FIG. 5.

As can be seen in FIG. 5, after osseointegration has taken place, there will be a relatively large area of bone to implant integration even though the penetration into the jaw bone is very short. The implant has first, circumferential surfaces 180, 182 which resist sideways movements of the dentures, while the second, lower surfaces 184, 185, 186 of the outer rim 30, upper face, and boss 28 resist vertical movements. The two surfaces combine to provide maximum rest factor to bone contact with a relatively short distance of penetration into the jawbone. The grooves 29 in the outer surface will resist rotational movements of the implant. Thus, the implant surfaces resist lateral and vertical loosening movements, and the implant effectively becomes fully integrated with the bone.

This implant is sufficiently short to be safely inserted even where some bone erosion has already taken place, with the appropriate height implant member and rest factor being selected according to the bone depth and tissue height of the particular patient.

The method of inserting the implant 12 in the jaw will now be described with reference to FIGS. 6–11 of the drawings. This can easily be done by a dentist or dental surgeon. First, a bore shaped to correspond to the shape of member 12 must be cut out. This is done using a series of special cutting burrs. A first water cooled burr or cutter (not illustrated in the drawings) is used to drill a cylindrical guide hole or pilot dimple at the center of a selected site, for example under the second molar area or at the distal end of a cantilevered bridge. The width of the alveolar crest with equal distance on both sides of the pilot dimple is then measured. The largest diameter rest factor implant which will fit within the available width while allowing at least ½ mm of bone on each side of the implant is selected. An internally irrigated implant body drill 44 of diameter matching that of the selected rest factor implant is then selected. Burr 44, illustrated in FIG. 6, has a smaller diameter pilot drill 46 for cutting out a cylindrical bore 48 and a larger diameter portion 50 having an end cutter 52 for drilling out the larger diameter upper end 56 of the bore. The cylindrical portion 50 may be provided with suitable markings or a scale (not shown) so that the dentist can control the depth the drilled bore. However, in the preferred version, the height of portion 50 matches the height of implant member 12. The length of the pilot drill 46 will correspond to the length of spigot 28 of the implant, so that spigot 28 will fit in bore portion 48. The dentist determines the optimum angle and drills in to the bone to a point where the larger diameter portion 50 ends.

Figure 7:
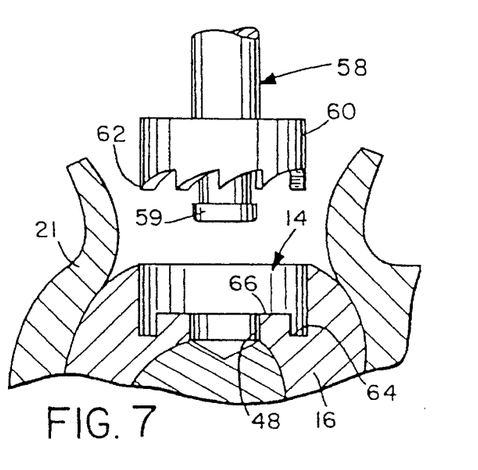
FIG. 7 is a similar view illustrating the final counter-boring operation for an implant.

FIG. 7 illustrates the operation of a water cooled guided core drill or burr 58 having a central guide or pilot tip 59 for fitting in the previously drilled bore portion 48 to center the tool on the bore. The tool has a cylindrical central body portion 60 having a downwardly facing annular ring of cutting teeth 62 for drilling out an annular groove or channel 64 around the periphery of the flat or shoulder 66 separating counter bore 56 from the smaller diameter bore portion 48. The length of the teeth controls the depth of groove 64, and will be equivalent to the height of the downwardly depending rim 30 of the implant to be received in the bore. Once the lower face of body portion 60 hits the flat 66, drilling is stopped.

All three cutting tools may be provided with a cage for collecting bone as it is drilled out of the bore. The collected bone may be used for filling any edges or spaces left after insertion of the implant.

After the bore for receiving the implant 12 has been prepared as described above, and debris has been cleaned out in the standard manner, for example by irrigating the site with sterile water or sterile saline, the implant 12 can be inserted. The healing screw 70 is initially secured to the implant.

Figure 8:
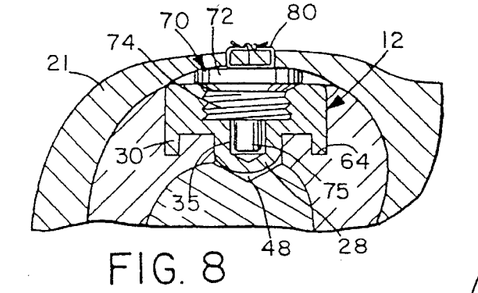
FIG. 8 is a similar view with an implant and healing screw in place and enclosed under tissue for the osseointegration period.

Prior to insertion in the previously prepared bore, the internal faces of the implant will be coated with a suitable bonding agent, such as hydroxyl apatite. These faces may be roughened as illustrated in FIGS. 1 and 3 to increase the bonding area and strengthen the adhesion in the bore 14. A suitable plastic insertion tool 67 (see FIG. 1) having a handle and a gripping end for snap engagement over the head of the healing screw is then used to insert the implant and attached healing screw in the bore. The bore is drilled out to a depth such that the upper end of the implant 12 will be at the bone level when fully inserted, as indicated in FIG. 8, or slightly below that level if desired. For convenience, the insertion tool is preferably a disposable, snap-off plastic member which is supplied in a sealed, sterile package together with the healing screw and implant, the three parts being supplied secured together in the package for easy handling. The insertion tool can be snapped off after the parts have been positioned in the bore.

The tissue or gum 21 is then secured over the implant and healing screw with conventional flap sutures 80. Since the head portion of the healing screw projecting above the implant member is relatively short, little or no bulge will be apparent when the tissue is sewn up. The site is left to heal for several months to allow the implant to osseointegrate, or bond with the surrounding bone. At this time, a special locating tool 82, best illustrated in FIGS. 4A, 9 and 10, is used to locate the implant.

The retrieval tool 82 comprises a central shaft 84 with a head or gripping handle 86 at one end. Handle 86 projects to one side of the shaft as indicated. A projecting probe 88 at the opposite end is designed for engagement in the bore 76 of healing screw. The probe has a sharp pointed end 91. A cutter sleeve or tissue punch 92 is slidably mounted on shaft 84. Cutter sleeve 92 has a projecting annular handle or gripping portion 94 and a lower cutting edge 96.

The use of the retrieval tool 82 to locate the implant site will now be explained, with reference to FIGS. 1 and 9. The approximate area of the implant is first located, utilizing radiographic charts and finger palpations. The pointed end 91 of the probe is then used to pierce the tissue 21 at the approximate site of the implant, and is then used as a probe to locate the upper face of the healing screw. Once the screw has been found, the concave recess (if provided) will act as a guide to direct the pointed end to the retrieval hole or bore 76 at the center of the healing screw, as illustrated in FIG. 9, centering the tool on the implant site.

Figure 9:
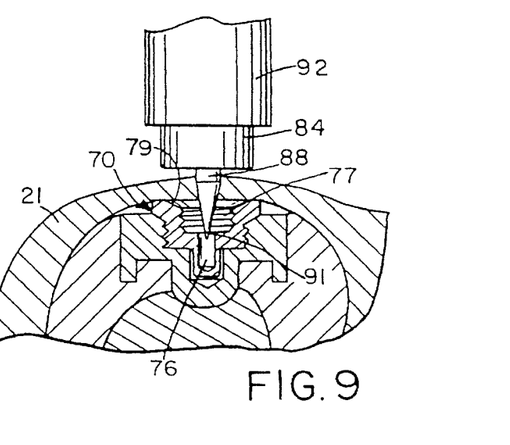
FIG. 9 illustrates the locating of the integrated implant under the issue.
Figure 10:
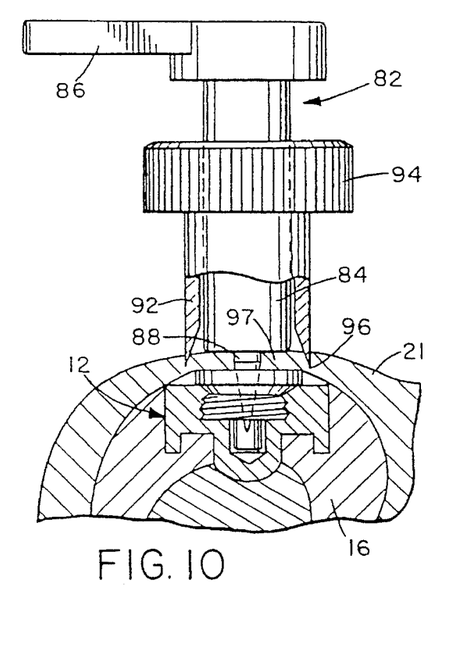
FIG. 10 illustrates the cutting out of a tissue plug overlying the healing screw.

Once the probe has entered bore 76, as illustrated in FIG. 9, the handle 86 of the locating tool is held firmly in one hand to support the tool upright and the tissue punch is turned in a circular motion while pushing it down along the locating tool with a firm pressure. The tissue punch is designed to cut out a plug 97 of tissue directly over the implant. The punch will be stopped when it engages the outer diameter of the healing screw. The locating retrieval tool 82 is then removed together with the tissue punch, simultaneously pulling out the plug of tissue. If the tissue plug does not pull out, it may be removed with forceps.

A separate healing screw removal tool 110 is then used to remove the exposed healing screw. Tool 110 is illustrated in FIG. 4B and 11, and comprises a shaft portion 112 with a head or gripping portion 114 at one end and a threaded portion 116 at the opposite end for threaded engagement in the threaded, upper end portion 77 of bore 76 of the healing screw. The threaded end 116 is threaded counter-clockwise into the healing screw, tightening the tool inside the healing screw and at the same time unscrewing the healing screw from the implant as illustrated in FIG. 11. The implant is thus exposed for secondary healing or restoration procedures.

This technique for exposing or recovery of an embedded implant after healing and osseointegration has taken place removes only a small plug of tissue from immediately above the implant site, avoiding the need to cut out an enlarged flap of the tissue both to locate the implant and to expose the healing screw for removal. Little or no suturing will be required. Thus, considerably less trauma to the tissue is involved, reducing the healing time and the risk of infection. Also, the healing screw is located and the tissue plug may be removed simultaneously with one tool, simplifying the procedure and reducing the time involved. The method involves the use of a specialized healing screw with a bore in its upper surface, together with a special locating and retrieval tool. It may be used not only for location of the implant 12 as described above, but also for locating any conventional cylindrical implants in implant dentistry, replacing the conventional healing screws of such implants with a healing screw as illustrated in FIG. 1 but having a stem or shaft designed for fitting into the implant bore. Although in the preferred embodiment described above, the upper end of the retrieval bore 76 in the upper face of the healing screw is screw threaded, it may alternatively be hexagonal with the retrieval tool having a corresponding hexagonal portion for mating engagement in the bore.

As an additional aid in locating the embedded implant, a thread or wire may be left projecting from the heading screw through the suture area, so that the location may be found easily after healing. Alternatively, the tissue overlying the implant may be marked with a suitable dye. However, it is expected that such markers will not normally be required, the dentist locating the general implant site by feel before piercing the tissue with the probe.

The same implant recovery tools may be used for any selected implant size, since the dimensions of bore 76 in the healing screw will be identical.

Once the healing screw has been removed and the exposed surface of the implant suitably cleaned and prepared, the appropriate rest factor 18 is inserted into the implant. The rest factor 18, in addition to providing a rest surface, also acts as a secondary tissue healing insert. The rest factor is selected with a head height so that it will project just above the patient's tissue level when installed. The shaft 38 of rest factor 18 is screwed into bore 32 of implant 12, as indicated in FIG. 5, with the mating surfaces first being coated with a suitable bonding agent.

Although the rest factor in the preferred embodiment has a head portion preformed in a range of heights, it may alternatively be provided with a longer extension piece which projects above the tissue level 20 when the member 18 is fully inserted. In this case, the dentist marks around the periphery of the selected member 18 at the tissue height, and removes the member from the implant. A suitable temporary cover or crown of a standard nature may be fitted into implant 12 at this point.

The dentist then mounts the member 18 in a previously prepared cast of the patient's jaw, and machines or cuts away the upper face of member 18 to provide the desired rest surface 22 at the tissue level 20, as determined by the markings made while the member was mounted in the patient's jaw. The cut away surface may be slanted or inclined according to the angle of the patient's tissue or gum. This allows the height to be customized for minimal side torque. The shape of the rest surface 22 may be of the dentists choice. For example, it may be concave, while the denture or prosthesis with which it is to cooperate has a corresponding convex area or bump 95 for fitting into the concave depression on the rest surface, so that the rest factor or member 18 accepts down pressure from the denture without any retention. However, in the preferred embodiment, members 18 with ready-made ball-shaped or other shape heads of various sizes in a range of tissue heights are provided to avoid the need for machining on site by the dentist.

This procedure may be utilized to implant one or more rest factors at any suitable location in the jaw, depending on the denture pressure points, for example as illustrated in FIGS. 12 and 13.

Figure 14:
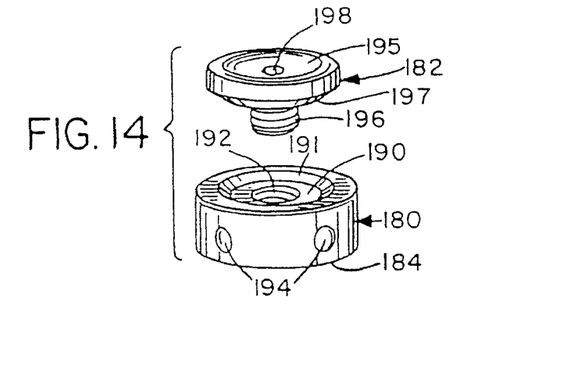
FIG. 14 is a perspective view of the separated implant and healing screw components of an implant assembly according to a second embodiment of the invention.

FIG. 14 of the drawings illustrates an alternative embodiment of the implant assembly which is much thinner than that of FIGS. 1–3 and 5 and which will therefore project only a minimal distance into the jawbone, further reducing the risk of interference with the nerve. This implant assembly is useful for providing a rest surface at a desired location in any patient's jaw, whether or not previous bone erosion is a factor, but is particularly useful in patients having significant bone erosion where very little depth is available for implants.

Figure 15:
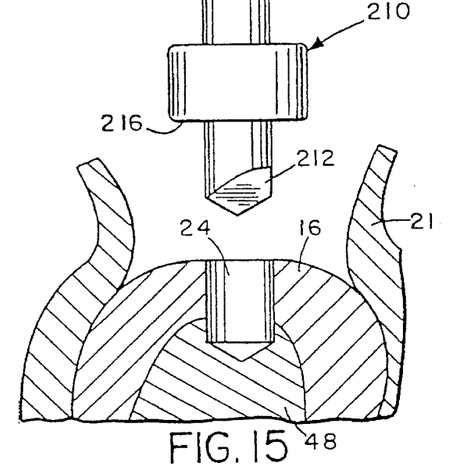
FIG. 15 is a jawbone section illustrating the initial drilling set up for the implant of FIG. 14.
Figure 16:
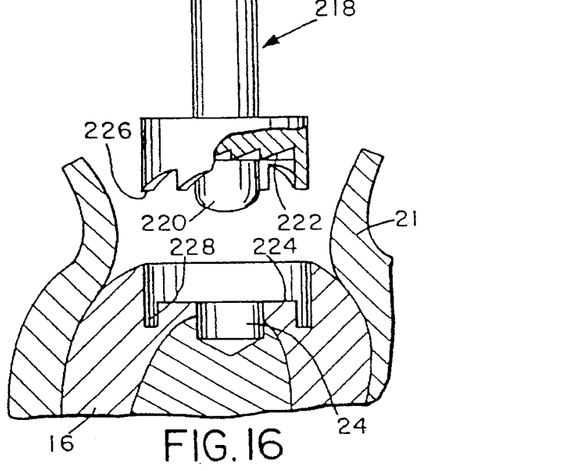
FIG. 16 is a similar view to FIG. 15 illustrating the next step in the drilling procedure.
Figure 17:
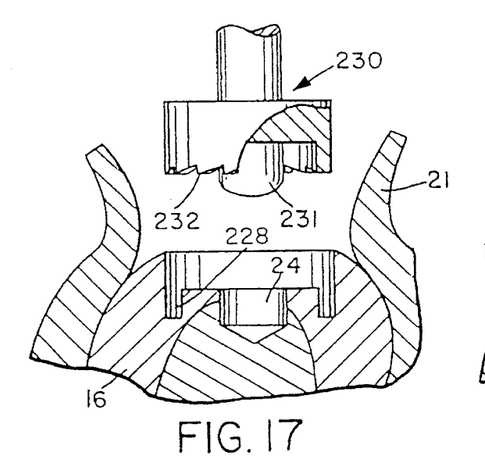
FIG. 17 is a similar view illustrating the finishing step in the boring operation.
Figure 18:
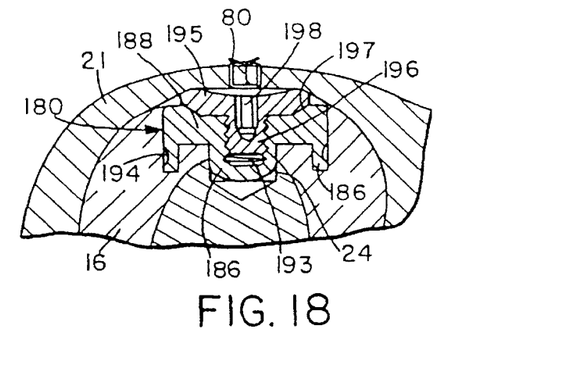
FIG. 18 is a similar view illustrating the implant and healing screw in place and enclosed under tissue for the osseointegration period.

FIG. 14 illustrates an implant member 180 and healing screw 182 of an implant assembly according to a second, modified embodiment of the invention. FIG. 18 illustrates the implant member 180 and healing screw 182 of FIG. 14 implanted in the jawbone during the osseointegration process, while FIGS. 15–17 illustrate a modified method of forming a bore in the jawbone for receiving the implant.

As illustrated in FIGS. 14 and 18, implant member 180 is a flat disc-like member having an undersurface of similar shape to the undersurface of member 12 in the first embodiment. However, the peripheral rim 184 and central spigot 186 are approximately the same length in this embodiment, so that the spigot 186 does not project downwardly below the lower end of rim 184. Preferably, member 180 has a total height of around 2 mm while its peripheral rim 184 projects around 1 mm below the undersurface of disc part 188. The member 180 is provided in a range of diameters, preferably 4.25 mm, 5 mm and 6 mm, for patients having varying alveolar ridge widths. As in the first embodiment, the maximum diameter possible implant member is selected for the patient dependent on the available space, i.e., the alveolar ridge width. The rim 184 is relatively thin, and in one particular example had a thickness of the order of 0.4 mm.

The member 180 has a recess 190 in its upper surface with a taper 191 extending around the outer periphery of the recess. A central, straight cylindrical bore 192 extends from the center of recessed area 190 into the spigot 186, and bore 192 has screw threads 193 extending along its length. Member 180 is made of the same material as the implant 12 of the first embodiment. As in the first embodiment, circular or rounded indents 194 are provided on the outer surface of member 180 to resist rotational movement after implantation. Between six and eight equally spaced indents may be provided, for example.

Healing screw 182 has a relatively short head portion 195 and a downwardly depending, screw threaded shaft portion 196 for mating engagement in the bore 192 of implant member 180, as illustrated in FIG. 18. The undersurface of head portion 195 seats in recessed area 190 and has a tapered annular surface portion 197 for seating on taper 191 around the recessed area 190, for accurate seating of the screw in bore 192. The upper surface of head 195 has a central, tool receiving bore 198 for receiving the end of a suitable tool for inserting the arrangement in a previously prepared bore in the jawbone, and also for receiving the end of locating tool 82 as described above in connection with the first embodiment of the invention. Bore 198 is of hexagonal cross-section, and is designed to be removed by a suitable removal tool having a hexagonal end after location by tool 82.

The rest factor or member of the second embodiment is not illustrated in the drawings but will be similar or equivalent to rest factor 36 as illustrated in FIGS. 2 and 5 of the drawings apart from its lower surface and downwardly depending shaft portion, which will be identical to lower surface and shaft portion of the healing screw 182 for mating engagement in the bore 192 in implant member 180 after osseointegration is complete.

The modified method of inserting insert member 180 in the jaw will now be described with reference to FIGS. 15–17 of the drawings. This procedure can easily be carried out by a dentist, although a dental surgeon may also perform the procedure if desired. After the tissue overlying the implant site has been cut, a pilot dimple is formed at the center of the selected site. The width of the alveolar crest or ridge at the implant site is measured, and the largest possible diameter implant which will fit within the available width while leaving at least ½ mm of bone on each side is selected.

A bore matching the selected implant dimensions is then accurately drilled out using a series of three internally irrigated drilling burrs. The first burr 210 has a straight pilot drill 212 for drilling out a cylindrical bore 214 to a desired depth at the implant site, as determined by stop 216, as illustrated in FIG. 15. Preferably, bore 214 will be slightly longer than the implant member, for example 3 mm. A second burr 218 is designed to cut out the desired bore shape to match the shape of the undersurface of implant member 180, as illustrated in FIG. 16. Burr 218 has a central, non-cutting guide or spigot 220 for fitting into previously drilled bore 214 for centering purposes, a first cutting surface 222 for cutting down to the level of flat 224, and an annular, downwardly projecting rim of cutting teeth 226 for cutting out part of annular recess 228 for receiving the annular rim 184 of the implant member. Preferably, teeth 226 are designed to cut recess 228 to a depth of ½ mm. The final burr 230 is illustrated in FIG. 17 and is designed to finish and smooth the surfaces of recess 228. Burr 230 also has a central guide 231 and an annular rim of finer cutting teeth 232 which cut the final ½ mm of the recess to a total depth of around 1 mm, and which smooth and finish the cut surfaces.

The finished bore of FIG. 17 is cut to very precise dimensions by the series of cutting drills so that the implant member can be accurately seated in the bore as illustrated in FIG. 18 after suitable treatment of the surfaces and application of bonding agents. The gap below spigot 186 does not affect the integration process and will soon fill in with bone. The accurate, close fitting of peripheral rim 184 into recess 228 provides great stability and resistance against any sideways movement during the three-month or more osseointegration period, so that a good bone-to-implant bond can be produced in spite of the minimal length of the implant.

After osseointegration is complete, the site is located and the healing screw 182 exposed and removed as described above in connection with the first embodiment of the invention. The rest factor (not illustrated) is inserted into the implant member as described in connection with the previous embodiment.

In both of the embodiments described above, the shape of the undersurface of the implant ensures that there will be little or no side sway either during or after the osseointegration period. This results from the downwardly projecting peripheral rim, having inner and outer circumferential surfaces which combine to resist any sideways forces. This resistance to side-sway is enhanced by the spigot 186 which also acts to resist sideways movement. The relatively large diameter of the implant provides a large area of downwardly facing surfaces which together resist downward forces on the implant assembly, further increasing the stability of the implant and acting to absorb biting pressures. The implant is selected to be of the maximum possible diameter according to the bone width available for implantation in a particular patient. The indents 29, 194 will act to resist rotational movements during and after osseointegration. The combined effect of the shape of the undersurface of the implant and its relatively large surface area is to produce a very stable implant with minimal penetration into the bone.

Although the implant member is illustrated as implanted so that its upper surface is at the bone level, it may be implanted to a lesser depth if the patient has a large amount of bone erosion or resorption. For example, if there is only 1 mm bone depth available for implantation without fear of interference with the nerve, the implant is simply installed to 1 mm in depth so that approximately 1 mm projects above the bone level. However, it will still have sufficient holding power to remain in position since the undersurface, and particularly the peripheral rim, will position the implant during osseointegration and bond to the surrounding bone to resist sideways and downwards forces. Since it is not anchored to any overlying body, upwards forces do not have to be resisted. Thus, sufficient bonding area is provided to resist any loosening during normal wear.

This implant system and method may be used in any implant procedure where a denture or prosthesis of more than one tooth is involved, and is particularly useful in posterior areas of the jaw where the implant depth is limited, for example the second molar area, and in conjunction with anterior implants or cantilevered bridges. The implant has a relatively short penetration into the bone, so that it can be installed in regions to the rear of the first bicuspid without fear of interference with the nerve, yet has sufficient anchoring surface area to integrate with the bone and accept down pressure of two to three hundred pounds from an overlying denture or prosthesis. Since the implant is not positively anchored to the prosthesis, it does not have to resist large upward or sideways forces, reducing the risk of bone erosion. At the same time, the rest factor will reduce the trauma to underlying tissue and reduce or eliminate bone erosion from the overlying denture by accepting the downward pressure from the denture.

The implant recovery method and tool described above will eliminate the need to locate and expose osseointegrated implants by a surgical flap technique. The locating tool and guided tissue punch accurately locate the implant with minimal trauma, and remove only a plug of tissue directly above the implant sufficient to expose the healing screw for removal. The amount of trauma and bleeding is reduced and the tissue around the implant site remains virtually intact.

Figure 19:
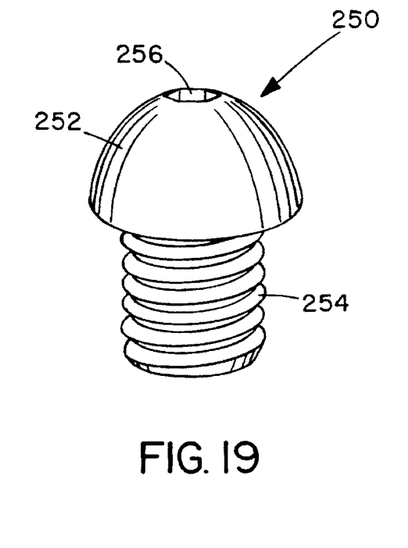
FIG. 19 is a perspective view of a rest factor according to another embodiment of the invention.

FIG. 19 illustrates a rest factor 250 according to another embodiment of the invention. The rest factor 250 is generally cylindrical and has an upper, dome-shaped portion 252 and a downwardly depending, threaded stem portion 254. The dome portion 252 has hex bore 256 formed in its upper end for gripping by a hex tool on installing or removing the rest factor 250, as will be explained in more detail below. The hex bore will be relatively small, preferably of the order of 0.050", and may be filled with a temporary sealant after installation.

The rest factor 250 is made from a suitable metal such as titanium alloy. The dome portion has a wear resistant titanium nitride coating applied. Rest factors are provided in a range of different dimensions. The dome portion is preferably provided in a range of different heights, and in a preferred embodiment rest factors were provided with dome portions of height 1.5 mm, 2.5 mm and 3.5 mm for fitting patients with different gum thicknesses. The total height of the rest factor is preferably in the range 2 mm to 4.5 mm.

Figure 20:
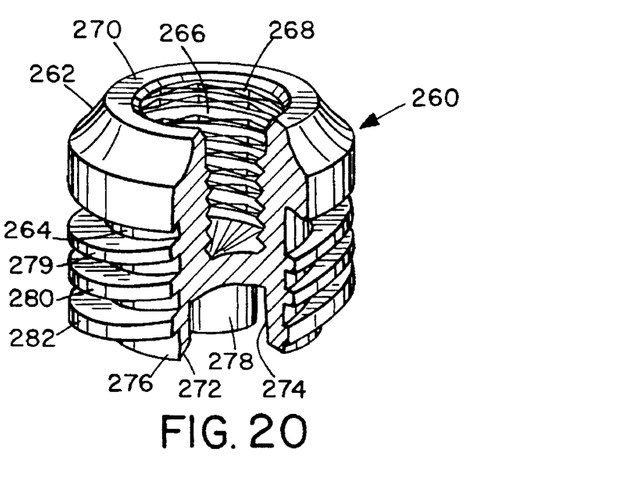
FIG. 20 is a perspective view, partially cut away, of one example of an implant for the rest factor of FIG. 19.
Figure 21:
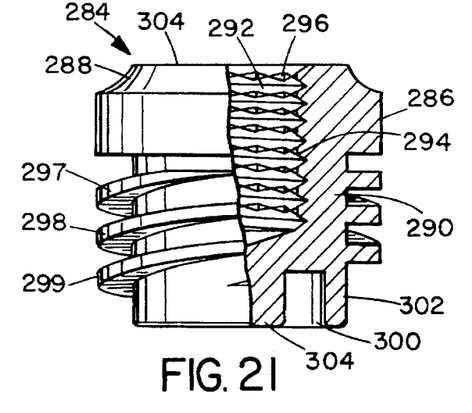
FIG. 21 is a side elevation view, partially cut away, of another implant with triple retaining threads.
Figure 22:
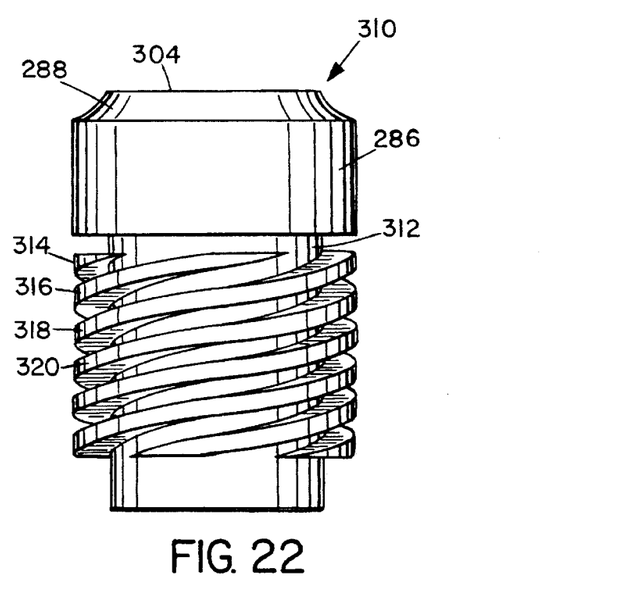
FIG. 22 is a side elevation view of a further implant with quadruple threads.
Figure 23:
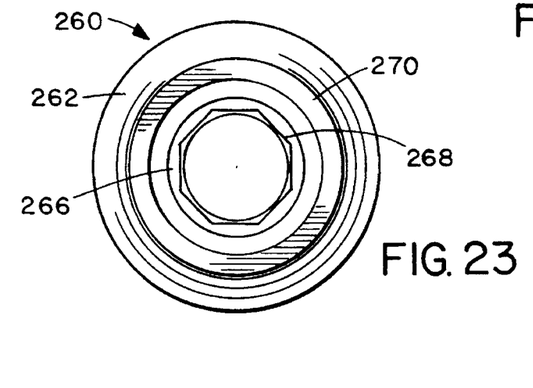
FIG. 23 is a top plan view of FIG. 20.

FIGS. 20, 21 and 22 illustrate three alternative types of implant for implanting in the jaw bone at a selected site to receive rest factor 250 or other denture fitting devices Such as denture anchors or magnetic abutments of a conventional type. The implant 260 of FIG. 20 is relatively short and has a body of generally cylindrical shape having an upwardly tapering upper end portion 262 and a downwardly depending stem portion 264. A threaded bore 266 extends downwardly from the upper end of the implant for receiving the threaded stem portion of the rest factor 250. An eight-sided cut 268 extends through the threads, as illustrated in FIGS. 20 and 23. The outer diameter of the implant at its upper end 270 is dimensioned to match the outer diameter of the dome portion of the implant at its lower end 272.

The stem portion 264 of the implant 260 has an annular recess 274 extending upwardly from its lower end to a position close to but offset downwardly from the lower end of the recess 268. Recess 274 forms an outer annular rim 276 and a central boss 278 at the lower end of the implant, and provides an area for bone growth and osseointegration upwardly into the implant. Thus, the implant is generally cup-shaped at its lower end, with a central protrusion in the cupped area. A triple lead screw having a first lead or thread 279, a second thread 280, and a third lead or thread 282 is formed around the outside of the stem portion 264. The threads 279, 280, 282 are preferably of square cross-section and project out a predetermined distance from the surface of the stem portion 264. The threads may each extend around approximately 180° and preferably do not overlap, although they may overlap in alternative embodiments.

FIG. 21 illustrates another implant 284 which is longer than that of FIG. 20. Again, the implant is generally cylindrical and has a relatively thin upper annular portion 286 with a short, upwardly projecting and tapered rim 288 and a downwardly depending stem portion 290 of reduced diameter. A bore 292 projects downwardly from the upper end of the implant 284 and has a threaded portion 294 for receiving the threaded stem of a rest factor member. A ten-sided or decagon cut 296 is formed through the threads, and preferably extends about halfway down the bore 292. In this version, the bore 292 projects downwardly into the stem portion of the implant, since the upper portion 286 and rim 288 are shorter than those of implant 260.

A triple lead thread having first, second and third threads 297, 298 and 299 is formed around the outer surface of stem portion 290. Preferably, the threads 297, 298 and 299 start at equally spaced intervals around the periphery of the stem portion adjacent its upper end but spaced downwardly a distance below the annular ring portion 286. The threads extend around the stem portion towards its lower end and terminate at a location spaced above the lower end of the stem portion. As in the version of FIG. 20, the stem portion 290 has an annular recess 300 at its lower end forming an annular rim 302 and central boss 304. As in the previous embodiment, the upper end 306 of the implant is of diameter matching that of the lower end of the rest factor.

FIG. 22 illustrates another, longer implant 310 which is similar to that of FIG. 21, apart from the fact that the stem portion 312 is longer and a quadruple lead screw is provided on the stem portion. The implant of FIG. 22 is otherwise identical to that of FIG. 21 and like reference numerals have been used for like parts. The implant has a bore identical to that of implant 284 extending downwardly from its upper end, and an annular recess at its lower end which is identical to the recess of implant 284. As in the previous two embodiments, the upper end 304 of the implant has a diameter matching that of the lower end of the dome portion of the rest factor.

A series of four separate threads 314, 316, 318 and 320 is provided around the periphery of the stem portion 312. The threads start at equally spaced intervals around the periphery of the stem at a location close to but spaced slightly below the upper end of the stem portion, to leave a gap between the annular ring 286 and the threads. The gap is in the range from 1 mm to 2 mm.

Although in the illustrated embodiment the implants 260 and 284 each have three threads, and the longest implant has four external threads, any one of these implants may have two, three or four threads. The double, triple or quadruple lead thread allows for quick and solid engagement into a tapped bone site. The projecting screw threads form an undercut region and bone growth and attachment in this area increases the strength of the attachment and resistance to loosening forces. The unique cup shaped recess design at the lower end of the implant is also designed to increase bone to implant surface contact and attachment area.

The pitch or angle of the thread is preferably relatively steep and is preferably in the range from around 9° to 17°. The spacing between adjacent threads is preferably at least 1 mm. It has been found that this is the minimum spacing required to ensure significant bone growth and osseointegration in the gaps between threads. The threads preferably project out around ½ mm from the surface of the stem portion of the implant, and they are about ½ mm in height. Thus, the gaps between the threads are twice as wide as the threads themselves. This provides good blood supply to the bone between the threads, and provides a greater bone thickness and stronger shelf of bone between the threads.

Both the implants and the rest factor are all made in a range of lengths and diameters to fit the size of different patient's jaws. Implants will be provided in a range of lengths. Preferably, the lengths are of the order of 2 mm, 4.5 mm, 7 mm, 10 mm and 13 mm. The 2 mm length implant will be of the type illustrated in FIG. 20, while the 4.5 mm implant will be of the type illustrated in FIG. 21 and the 7 mm, 10 mm and 13 mm implants will be as illustrated in FIG. 22. Each of the different implants will be provided in a range of different outer diameters, preferably 4 mm, 5 mm and 6 mm. Preferably, the height of the tapered rim of the implant 260 or 310 is as short as possible, for example around 0.5 mm.

The implants are made of a suitable material such as titanium and may be coated with a coating of a material for improving bone adhesion.

The method of installing implants 260, 284 and 286 will be similar with appropriate changes in the dimensions of the drilled bore to accommodate the different length stem portions and numbers of threads. The method will therefore be described for the implant 260 only, by way of example. The implantation method is similar to that illustrated in FIGS. 6–11 and described above.

The first step in the implant procedure is to select the site in the jaw at which the implant is to be installed. The appropriate height and diameter implant member is selected dependent on the bone depth, tissue height, and jaw thickness at the selected site. The minimum bone depth required is 1 mm between the bottom end of the installed implant and the mandibular nerve canal or maxillary sinus space. Thus, the total bone depth required for installing the 2.5 mm implant is only 3.5 mm, while the longer implants can be installed where a greater bone depth is available. The minimum bone width required to place a rest factor implant is ½ mm each on the lingual and facial sides of the implant, requiring a 5.0 mm total ridge width for the 4.0 diameter implant, 6.0 mm ridge width for the 5.0 mm diameter implant, and 7.0 mm ridge width for the 6.0 mm implant. Based on these dimensions, the appropriate implant can be selected.

The very short, 2.5 mm implant can be installed safely even where some bone erosion has already taken place and even in the distal jaw regions without risking interference with the mandibular nerve. The design is such that the implant has a relatively large surface area for bone to implant osseointegration, and undercut areas for improved retention and resistance to movement in any direction.

Once the appropriate implant has been selected, a bore shaped and dimensioned to correspond to the shape and dimensions of the implant is cut out. This is done in a series of steps. First, a mesio-distal incision is made through the tissue or gum 321 along the alveolar mid-crest at the selected site, typically the area of the second molar. A bone plateau is created which is made as flat as possible by removing ridges or other bone irregularities. At this point, the width of the alveolar crest can be measured to determine the largest diameter rest factor implant which can be fitted within the available width and still allow at least ½ mm of bone on each side. The implant is placed as close as possible to the lingual side while still allowing the ½ mm of bone on the lingual side.

Figure 24:
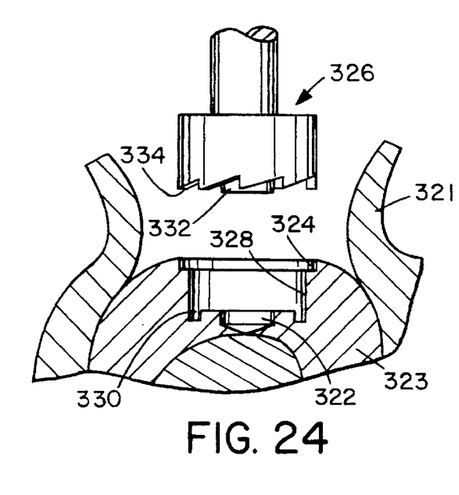
FIG. 24 is a view similar to FIG. 7, showing the addition of a shallow counter-bore.

At this point, a pilot burr is used to drill out a pilot hole of appropriate depth at the center of the insertion site, as illustrated in FIG. 15 above. The pilot hole diameter will be substantially identical to the diameter of the implant central boss 278. An appropriate depth limiting sleeve is used with the pilot burr in order to limit the depth of the pilot hole to match the implant height. Thus, depth limiting sleeves will be provided for each of the four different implant heights, and the appropriate sleeve will be selected on installation. The lower end of a previously drilled pilot hole 322 in jawbone 323 can be seen in FIG. 24, which illustrates a subsequent step in the procedure.

An alignment pin may be placed in the pilot hole to check for proper alignment to the path of a prosthetic insertion and between multiple implants.

After alignment, a spot-face drill (not illustrated) is used to make a shallow, 360° shoulder or seat 324 into the crest of the bone. This seat is used to assist in engaging of a bone tap in a later stage of the procedure. The drill is withdrawn several times during site preparation to remove bone buildup between the flutes of the drill. An implant body drill is used to drill out the main recess 328 for receiving the implant. This drill will be similar to drill 44 illustrated in FIG. 6, above, and will have a diameter corresponding to that of the stem portion of the selected implant. Thus, the drill will have a diameter equal to the implant diameter less the thickness of the threads, or 4.0 mm in the case of a 5.0 mm implant, for example.

In the next step of the procedure, a core drill 326 is used to cut an annular ring or recess 330 at the bottom of recess 328 for receiving the underside rim 272 of the implant. Drill 326 has a central guide 332 for centering in the previously drilled pilot hole 322, a cylindrical central body portion, and a downwardly facing annular ring of cutting teeth 334 for drilling out an annular groove or recess 330 for receiving the rim 272 (or 302 in the case of the implant 284 or 310) of the implant.

Figure 25:
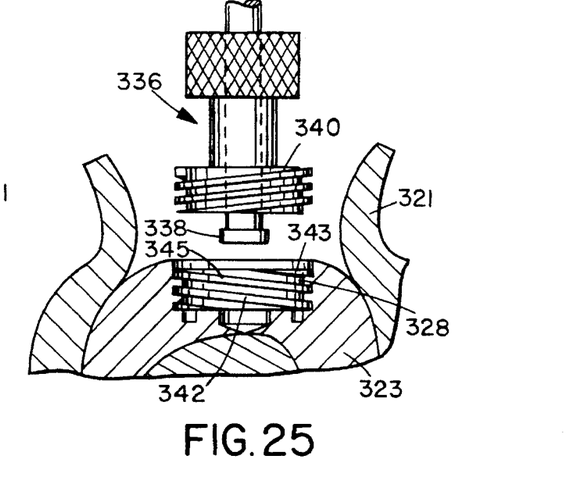
FIG. 25 is a similar view showing the cutting of threads to receive an implant.

A series of three guided hand taps (starting tap, intermediate tap and finish tap) are used to make a multiple lead tapped preparation into the drilled hole 328. It will be understood that the triple and quadruple leads will be made in a similar manner. One of the thread taps 336 is illustrated in FIG. 25. Each tap has a tap guide pin 338 which engages the pilot bore to keep the tap centered on the recess. Optionally, a tap guide template (not illustrated) may be secured across the recess via pins secured on opposite sides of the implant site. This can be used to provide better support for the bone tap if the patient has spongy, cancellous bone. The tap 336 has triple lead cutting flutes 340 for forming a thread matching that on the insert. The starting tap has a machined line indicating the start of the double cutting edge of the bone tap. The starting tap is positioned into the drilled recess and the cutting flutes are engaged into the cortical bone, with the machined line on the tap positioned perpendicular to the longitudinal axis of the ridge. The implant site is then hand tapped and threads 342, 343 and 345 are tapped into the recess. The tap is backed off a quarter of a turn several times during the process to clear bone chips. In this way, the tap is worked down to the bottom of the drilled recess 328.

The procedure is then repeated using an intermediate tap, which will be marked with two lines to distinguish from the other two thread cutting taps. The lines are positioned in the same starting position as the line on the starting tap. Finally, the procedure is repeated with the finish tap, which will be marked with three lines, to create a final cut of the bone thread to accept the implant.

Figure 26:
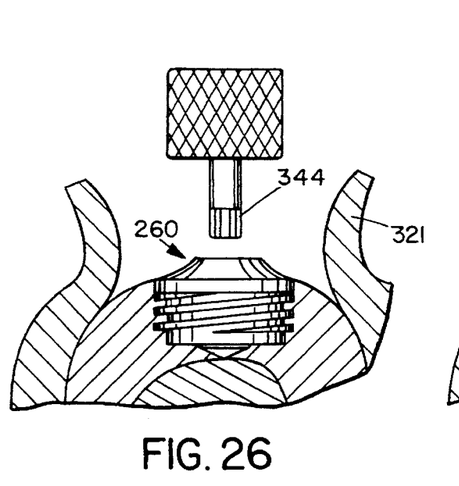
FIG. 26 is a similar view showing insertion of the implant.

An octagonal wrench 344 is used to place the implant into the prepared implant recess, as illustrated in FIG. 26. The octagonal end of wrench 344 will engage in the octagon 268 cut through the threads 266 and will not damage the threads in bore 266. The implant is completely seated with the implant threads completely engaged in the bone threads and the tapered upper portion of the implant projecting above the level of the bone, as illustrated in FIG. 26. If the implant is set in correctly, the stem portion 264 will have its upper end located ½ to 1 mm below the top of the bone, as illustrated in FIG. 26.

A healing screw is then threaded into the implant to protect the internal threads of the implant during the osseointegration period. The healing screw is similar to the healing screw 70 of the first embodiment but with a threaded stem matching bore 266 and a hex hole in place of threaded hole 76 at the upper end of the screw. The flap of gum 321 is sewn down over the implant site, in a similar manner to that illustrated in FIG. 8 above, after installation of the healing screw.

The implant is then left for a healing period to allow the bone to osseointegrate with the surface of the implant. A healing period of not less than 4½ months should be used. The bone will grow over and osseointegrate into the gaps between the threads, providing a greater osseointegration surface area and better retention of the implant. The cup-shaped design of the lower end of the implant, along with the multiple lead threads, increases bone to surface contact and helps to withstand posterior occlusal load.

Where a triple or quadruple lead thread is used, resistance to rocking or movement of the implant is provided. With two opposing threads, there may be some tendency for the implant to rock from side to side. Thus, implants with three or four threads are used for even greater resistance to rocking as a result of loads.

After the minimum period required for osseointegration, an incision is made over the implant for access to the healing screw. Radiographic charts and finger palpation may be used to locate the general area of the implant. The incision may be made in a conventional manner, but preferably a guided tissue punch 82 is used as in the previous embodiments. The tissue is pierced with the sharp point or probe 91 of the tissue punch, and the implant site is probed until the point 91 locates a hex hole provided on the top of the healing screw. The guided tissue punch 92 is then turned down on the guide with firm pressure until it punches an opening through the tissue or gum. The tissue punch will engage the outside diameter of the healing screw, and will cut out a plug of tissue directly over the center of the implant, as illustrated in FIG. 10 above.

The locating tool/tissue punch assembly is then removed, simultaneously pulling out the cut plug of tissue. If the tissue does not pull out with the tissue punch, forceps may be used to remove it and expose the healing screw. A cover screw hex tool (not illustrated) is used to engage the hex hole at the top of the cover screw and remove the cover screw from the implant.

Figure 27:
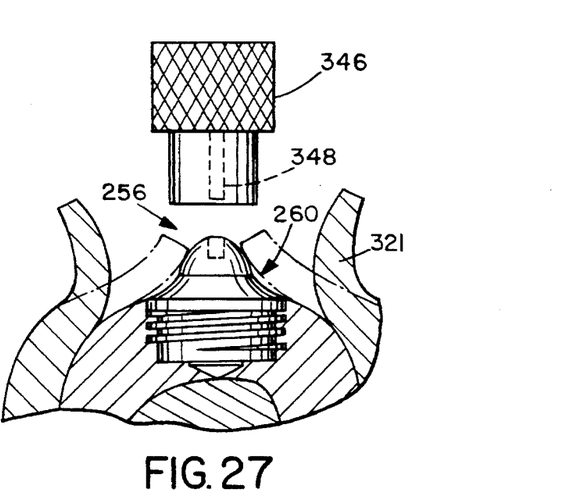
FIG. 27 is a similar view showing attachment of the rest factor.

The implant is now exposed for attachment of the dome-shaped rest factor 250 as illustrated in FIG. 27. The implant may alternatively be attached to other dental devices, such as implant anchors or magnetic abutments for dentures. The dimensions of the selected rest factor will depend on the implant dimensions and also the tissue height of the patient. The height of the implant should be such that the top of the dome is at the tissue level or only slightly above it. The dome portion of the rest factor selected should therefore have a height substantially equal to the tissue or gum thickness. If the gingival layer has a height substantially greater than the largest dome portion, tissue reduction must be used to reduce the gingiva thickness to a maximum of 3 mm at the implant site.

Once the correct size rest factor has been selected, a hex wrench 346 having a hexagonal shaft 348 is used to engage the hex bore 256 at the upper end of the dome-shaped upper end portion 252 of the rest factor. The rest factor is then threaded into the bore of the implant, as illustrated in FIG. 27. The tissue is then sewn back around the implant dome, as indicated in dotted lines in FIG. 27, and the dome is left in place for around 4–6 weeks to allow for a period of reduced implant loading during gingival healing. The patient's denture should be fitted to the dome top with a soft reline material to maintain proper occlusion during the gingival healing period. This is done by taking a full arch reline impression including the exposed metal tip of the rest followed to prepare a master cast of the jaw including the exposed tip of the dome. The denture base is relined using this cast in the normal manner.

If a change in tissue height has occurred during the tissue healing period, the rest factor may be unthreaded and replaced with another rest factor of the correct dimensions.

Once the healing period is complete, the top of the dome is exposed for a prosthesis to rest on with lateral freedom of movement. The preferred arrangement is to use the dome as a permanent, non-retentive rest when the patient has existing anterior retention for a prosthesis. However, the rest factor may be used as an attachment if required, for example if there is no existing retentive means for the prosthesis, or lateral stability is needed due to severely reduced ridge height. A hole is drilled into the center of the dome to an appropriate depth, and resin is injected into the counter-bore. When the resin starts to become firm, a post forming part of a standard rest plate of a denture is inserted into the bore until the bottom of the plate comes into contact with the resin.

Figure 28:
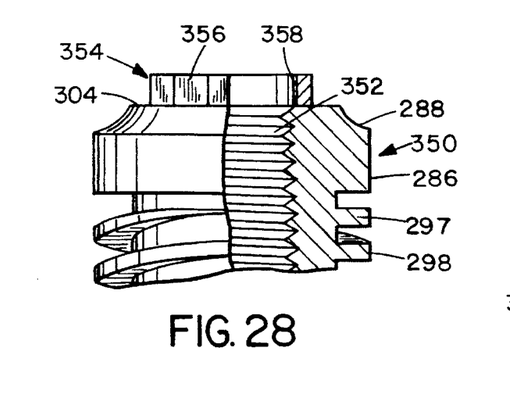
FIG. 28 is a side elevation view, partially cut away, of another modified implant having an alternative wrench element.
Figure 29:
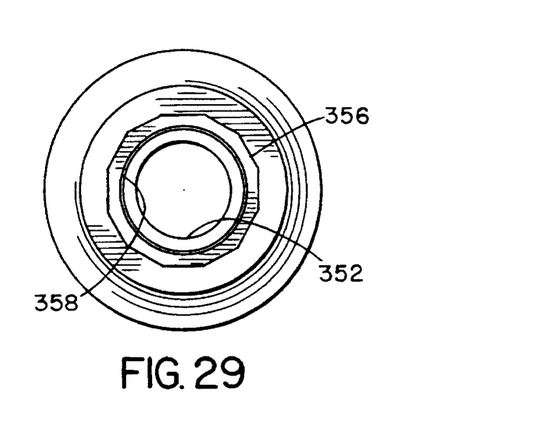
FIG. 29 is a top plan view of the implant of FIG. 28.

FIGS. 28 and 29 illustrate a modified insert 350 for use with a rest factor 250 in an equivalent manner to that described above. However, rather than having a multi-faceted cut for receiving a wrench in the threaded bore 352 of insert 350, an external, twelve-sided wrench element 354 is secured to the upper end of insert 350. Element 354 has an outer twelve-sided surface 356 for engaging a wrench with a corresponding internal bore, and a through bore 358 coaxial with threaded bore 352 but of larger diameter. Element 354 is preferably formed separately from insert 350 and then pressure bonded or welded to it. A conventional hex wrench may also be used to engage the element 354.

Apart from threaded bore 352 and wrench element 354, insert 350 is otherwise identical to that of FIG. 21 and like reference numerals have been used as appropriate. It will be understood that a wrench element 354 may also be provided on the insert of FIG. 20 or FIG. 22 in place of the multi-sided internal cut. This avoids the need for a precision machined cut extending through the threads, where the cut must be of precise dimensions between those of the inner and outer diameter of the threads to avoid damaging the threads.

The use of an implant having two or more stabilizing threads on the outer surface of the stem embedded in the jawbone, combined with the inverted cup shape of the lower end of the implant, provides a stable implant which resists movement even in the case of the very short version. Bone growth into the inverted cup and between the threads provides a large area of bone to implant contact and osseointegration, providing significant resistance to both lateral and downward forces both during and after the osseointegration period.

The non-retentive rest factor can be used to support dentures non-retentively in the posterior area of the jaw. As a result, the pressure applied to the lower jaw by the denture during mastication is dramatically reduced, reducing the discomfort and bone erosion normally resulting from denture wear. Although the implant can be installed anywhere in the jaw for retentive or non-retentive engagement with a denture or prosthesis, it is particularly useful for providing support in posterior regions of the jaw where the jawbone has become eroded. The accepted formula for cantilevered dentition attached to anterior implants limits the extension of the cantilever over the posterior ridge to no further than the distance between the plane of the most anterior implant and the furthest posterior implant. This results in a lack of support under the molar dentition and an extraction effect on the anterior implants during masticatory function. With the additional support provided by one or more rest factors and implants in posterior regions of the jaw, the extraction effect is significantly reduced or eliminated. In addition, trauma to the ridge under occlusal load, and the resulting bone loss, may be reduced.

Although some preferred embodiments of the present invention have been described above by way of example only, it will be understood by those skilled in the field that modifications may be made to the disclosed embodiments without departing from the scope of the invention, which is defined by the appended claims.

I claim:

1. A dental implant assembly for supporting as a rest factor the distal end of a denture anchored elsewhere in the jaw, comprising:

implant means for embedding in the distal region of the jawbone including a first part for projecting into and osseointegrating with the jawbone and a second part for projecting up to just above the tissue level;

the first part being relatively thin and having a predetermined height less than the distance between the top of a patient's jawbone at the implant site and the underlying region of the mandibular nerve;

the second part having an upper rest surface for supporting but not being connected to overlying portions of a denture anchored elsewhere in the jaw to resist biting pressure on the tissue and bone; and the first part comprising a thin disc-shaped member having a downwardly projecting annular rim and a central spigot projecting downwardly from the disc-shaped member.

2. The assembly as claimed in claim 1, wherein said first part comprises an implant member and the second part comprises a rest factor releasably securable to the implant member.

3. The assembly as claimed in claim 2, including a plurality of implant members in a range of different sizes, the members having outer diameters in the range from about 4.25 to 6 mm.

4. The assembly as claimed in claim 2, including a plurality of implant members in a range of different heights from 2 to 4.5 mm.

5. The assembly as claimed in claim 1 wherein the first part has a height no greater than its diameter.

6. The assembly as claimed in claim 1, wherein the first part has a selected diameter slightly less than the width of the alveolar crest at the implant site.

7. The assembly as claimed in claim 6, wherein the selected diameter is 1 mm less than the width of the alveolar crest.

8. The assembly as claimed in claim 1, wherein the first part has a height no greater than 4.5 mm.

9. The assembly as claimed in claim 8, wherein the first part has a height of between 2 to 4.5 mm.

10. The assembly as claimed in claim 1, wherein the rest surface has a shaped, cooperating area for non-retentive seating engagement with a correspondingly shaped mating surface on an overlying denture.

11. The assembly as claimed in claim 1, wherein the first part has a central bore in an upper face of the disc-shaped member.

12. The assembly as claimed in claim 11, wherein the second part comprises a shaft portion for engagement in the central bore of the implant member and a solid head portion projecting upwardly from the shaft portion.

13. The assembly as claimed in claim 12, wherein the extension portion is generally cylindrical with an upper, convex rest surface.

14. The assembly as claimed in claim 11, wherein the bore has an upper threaded portion and a non-threaded, lower extension portion, the second part having a shaft portion with a corresponding threaded upper portion and non-threaded lower portion for mating engagement in said implant member bore.

15. The assembly as claimed in claim 14, wherein said implant member bore and rest factor shaft portion have upper ends having matching tapers.

16. A dental implant assembly for supporting as a rest factor the distal end of a denture anchored elsewhere in the jaw, comprising:

implant means for embedding in the distal region of the jawbone including a first part for projecting into and osseointegrating with the jawbone and a second part for projecting up to just above the tissue level;

the first part being relatively thin and having a predetermined height less than the distance between the top of a patient's jawbone at the implant site and the underlying region of the mandibular nerve;

the second part having an upper rest surface for supporting but not being connected to overlying portions of a denture anchored elsewhere in the jaw to resist biting pressure on the tissue and bone;

the first part comprising a thin disc-shaped member having a downwardly projecting annular rim; and axially extending spaced grooves in the outer surface of the annular rim for restricting rotation of the embedded implant.

17. A dental implant assembly for supporting as a rest factor the distal end of a denture anchored elsewhere in the jaw, comprising;

implant means for embedding in the distal region of the jawbone including a first part for projecting into and osseointegrating with the jawbone and a second part for projecting up to just above the tissue level;

the first part being relatively thin and having a predetermined height less than the distance between the top of a patient's jawbone at the implant site and the underlying region of the mandibular nerve;

the second part having an upper rest surface for supporting but not being connected to overlying portions of a denture anchored elsewhere in the jaw to resist biting pressure on the tissue and bone;

the first part comprising a generally cylindrical member having a downwardly depending annular rim, and a central spigot projecting downwardly from the cylindrical member, the central spigot having a length in the range from 1 to 2 mm.

18. A combined denture and support assembly, comprising:

a denture of more than one tooth;

an anchor securing one end of the denture to the jawbone;

support means for freely supporting a distal region of the denture at a selected location to the rear of the first bicuspid, the support means comprising a first part for embedding in the jawbone at the selected location and a second part for projecting up to at least the tissue level, the second part having an upper rest surface for supporting but not being connected to the denture and for accepting biting pressure from the denture; and the first part comprising a thin disc-shaped member having a downwardly projecting annular rim and a central spigot depending downwardly from the disc-shaped member to define an annular cavity between the spigot and rim.

19. The assembly as claimed in claim 18, wherein said first part extends no more than about 4 mm into the jawbone.

20. The assembly as claimed in claim 19, wherein said first part has a diameter in the range from 4 mm to 6 mm.

21. The assembly as claimed in claim 18, wherein said second part extends up to between ½ to 1 mm above the tissue level.

22. The assembly as claimed in claim 18, wherein the first part comprises a flat, disc-shaped member having a downwardly projecting peripheral rim.

23. The assembly as claimed in claim 22, wherein the first part has a height of 2 mm and the rim projects 1 mm below the undersurface of the disc-shaped member.

24. A dental implant assembly for embedding in the jawbone of patient, comprising:

an implant member for embedding in and osseointegrating with the jawbone of a patient at a selected site;

an attachment member for securing to the implant member after osseointegration;

the implant member having an upper end portion with a central bore, the attachment member and central bore of the implant member having interengageable securing means for releasably securing the attachment member to the implant member, and a stem portion depending downwardly from the upper end portion for engagement with a recess in the jawbone of shape and dimensions matching those of the stem portion;

the stem portion having an annular indent at its lower end;

the stem portion having outwardly projecting screw threads; and the threads comprising multiple lead threads.

25. The assembly as claimed in claim 24, wherein the threads comprise triple lead threads.

26. The assembly as claimed in claim 24, wherein the threads comprise quadruple lead threads.

27. The assembly as claimed in claim 25, wherein the threads are of square cross-section.

28. The assembly as claimed in claim 24, wherein the spacing between adjacent threads is at least 1 mm and the threads run parallel to one another.

29. The assembly as claimed in claim 28, wherein the gap between adjacent threads is larger than the width of each individual thread.

30. The assembly as claimed in claim 24, wherein the threads project out to a distance of ½ mm from the surface of the stem portion.

31. The assembly as claimed in claim 24, wherein the stem portion has an upper end and a lower end and the threads start at a position spaced below the upper end of the stem portion.

32. The assembly as claimed in claim 31, wherein the threads terminate at a position spaced above the lower end of the stem portion.

33. The assembly as claimed in claim 24, wherein the central bore projects downwardly into the stem portion of the implant member.

34. The assembly as claimed in claim 24, wherein the upper end portion of the implant member comprises an annular ring and an inwardly tapering rim projecting upwardly from the annular ring.

35. The assembly as claimed in claim 24, including a wrench element projecting from the upper end portion of said insert member for engagement with a tool for inserting the implant member, the wrench element having a bore aligned with the central bore of said insert member.

36. The assembly as claimed in claim 35, wherein the wrench element has a twelve-sided outer wrench engaging surface.

37. The assembly as claimed in claim 24, including a plurality of implant members in a range of different heights from 2 to 13 mm.

38. A dental implant assembly for embedding in the jawbone of patient, comprising:

an implant member for embedding in and osseointegrating with the jawbone of a patient at a selected site;

an attachment member for securing to the implant member after osseointegration;

the implant member having an upper end portion with a central bore, the attachment member and central bore of the implant member having interengageable securing means for releasably securing the attachment member to the implant member, and a stem portion depending downwardly from the upper end portion for engagement with a recess in the jawbone of shape and dimensions matching those of the stem portion;

the stem portion having an annular indent at its lower end; and the attachment member comprising a rest factor member having an upper rest surface for supporting, but not being connected to, overlying portions of a denture anchored elsewhere in the jaw, the rest factor member having an upper, dome-shaped portion and a downwardly depending stem portion for engagement in said implant member bore, the rest surface comprising the upper end of said dome-shaped portion.

39. The assembly as claimed in claim 38, including a plurality of rest factor members having dome-shaped portions of different heights in the range from 1.5 mm. to 3.5 mm.

40. The assembly as claimed in claim 39, in which said rest factor members have total heights in the range from 2 mm. to 4.5 mm.

41. The assembly as claimed in claim 38, wherein said dome-shaped portion has a hex indent at its upper end for engagement with a hex tool for insertion of the rest factor member into an implant member bore.

42. An implant member for embedding in a patient's jawbone for attachment to other dental devices, the member comprising:

a generally cylindrical body having an upper end portion for projecting above the jawbone and a lower stem portion for insertion in a recess prepared in a patient's jawbone;

the upper end portion having a central bore for insertion of a portion of a dental device to be attached to the implant member; and the lower end portion having an outer cylindrical surface and a plurality of multiple lead threads projecting outwardly from the outer surface.

43. The implant member as claimed in claim 42, wherein the upper end portion includes a cylindrical ring portion of diameter greater than said cylindrical surface of the lower end portion, and an inwardly tapered rim portion projecting upwardly from said ring portion.

44. The implant member as claimed in claim 43, wherein said ring portion has a diameter equal to the diameter of said threads.

45. The implant member as claimed in claim 43, wherein said upper end portion has a height less than that of the lower end portion.

* * * * *